(12) United States Patent
Gibbs et al.

(10) Patent No.: US 12,030,842 B2
(45) Date of Patent: Jul. 9, 2024

(54) ALKYL-SUBSTITUTED HYDROXYAROMATIC COMPOUNDS WITH HIGHLY STRUCTURED ALKYL BRANCHES

(71) Applicants: CHEVRON ORONITE COMPANY LLC, San Ramon, CA (US); CHEVRON U.S.A. INC., San Ramon, CA (US)

(72) Inventors: Andrew R. Gibbs, Novato, CA (US); Sven Ivar Hommeltoft, Pleasant Hill, CA (US)

(73) Assignees: CHEVRON ORONITE COMPANY LLC, San Ramon, CA (US); CHEVRON U.S.A. INC., San Ramon, CA (US)

(*) Notice: Subject to any disclaimer, the term of this patent is extended or adjusted under 35 U.S.C. 154(b) by 0 days.

(21) Appl. No.: 17/798,450

(22) PCT Filed: Feb. 11, 2021

(86) PCT No.: PCT/IB2021/051102
§ 371 (c)(1),
(2) Date: Aug. 9, 2022

(87) PCT Pub. No.: WO2021/161199
PCT Pub. Date: Aug. 19, 2021

(65) Prior Publication Data
US 2023/0090561 A1  Mar. 23, 2023

Related U.S. Application Data

(60) Provisional application No. 62/976,406, filed on Feb. 14, 2020, provisional application No. 62/977,526, filed on Feb. 17, 2020.

(51) Int. Cl.
*C07C 39/06* (2006.01)
*C10M 129/10* (2006.01)
*C10N 20/00* (2006.01)

(52) U.S. Cl.
CPC ........... *C07C 39/06* (2013.01); *C10M 129/10* (2013.01); *C10M 2205/0245* (2013.01); *C10M 2207/024* (2013.01); *C10N 2020/071* (2020.05)

(58) Field of Classification Search
CPC .... C09K 8/584; C09K 8/588; C09K 2208/34; C07C 37/14; C07C 39/06; C10M 129/10;
(Continued)

(56) References Cited

U.S. PATENT DOCUMENTS

| 4,814,540 A * | 3/1989 | Watanabe | C07C 2/34 585/512 |
| 2008/0269351 A1* | 10/2008 | Campbell | C10M 129/10 514/731 |
| 2011/0124539 A1* | 5/2011 | Sinquin | C10M 159/22 508/567 |

FOREIGN PATENT DOCUMENTS

| EP | 0718393 | 6/1996 |
| WO | 2011063113 A2 | 5/2011 |
| WO | 2015183685 | 12/2015 |

* cited by examiner

*Primary Examiner* — Vishal V Vasisth

(57) ABSTRACT

The present disclosure provides a hydroxyaromatic product. The alkyl hydroxyaromatic compound having a structure given by (Continued)

where R is a hydroxyaromatic group, X is hydrogen or methyl group and where n is 1 or greater.

23 Claims, 1 Drawing Sheet

(58) Field of Classification Search
CPC .... C10M 2207/024; C10M 2205/0245; C10M 2207/023; C10N 2020/071
See application file for complete search history.

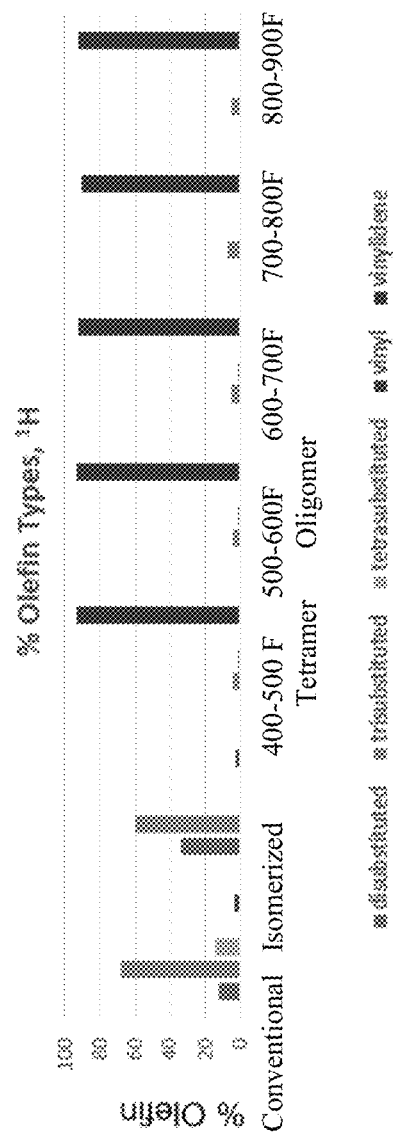

ALKYL-SUBSTITUTED HYDROXYAROMATIC COMPOUNDS WITH HIGHLY STRUCTURED ALKYL BRANCHES

This application is a 371 of PCT/IB2021/051102, filed Feb. 11, 2021 PCT/IB2021/051102 has PRO of 62/977,526, filed Feb. 17, 2020 and PCT/IB2021/051102 has PRO of 62/976,406, filed Feb. 14, 2020.

TECHNICAL FIELD

This disclosure relates to commercial alkyl-substituted hydroxyaromatic products. More specifically, this disclosure describes compositions and methods for preparing alkyl-substituted hydroxyaromatic additives having highly-structured alkyl groups and lubricating oil compositions containing the same.

BACKGROUND

Alkyl-substituted hydroxyaromatic compounds (e.g., alkylphenols) can be used to prepare a number of commercial products including detergents, emulsifiers, pesticides, fragrances, thermoplastic elastomers, antioxidants, and surfactants. For example, alkylphenols can be used to synthesize sulfurized alkyl-substituted phenate compounds that are useful as detergents in lubricating oils. One issue is the potential toxicity of alkylphenols to the environment. Certain alkylphenols such as tetrapropenyl phenol (TPP) are now classified as reproductive toxins. In the lubricating oil industry, residual presence of TPP as unsulfurized alkyl-substituted phenate byproducts during detergent synthesis is a concern.

Another issue specific to TPP relates to its synthesis which involves the alkylation of phenols with propylene oligomers. In a conventional synthesis, phenol molecules are alkylated with propylene oligomers that are rich in propylene tetramers with highly chaotic non-linear structure and highly substituted internal double bond (e.g., tri- and tetra-substituted). The crowded structure of propylene tetramers is possibly one main reason why the alkylation reaction requires several days to proceed and large excess of propylene tetramers.

In an effort to address these ongoing issues, alternative olefins have been identified as potential replacements for propylene tetramers. In particular, structurally isomerized linear alpha olefins have been used in the production of commercial alkylphenol detergents. However, an isomerization step adds to the already high cost of linear alpha olefins while resulting in less active internal olefins. Moreover, alkylphenol products made from isomerized linear alpha olefins often perform relatively poor in lab tests, possibly due to inadequate methyl branching.

Other efforts have focused on utilizing polyisobutylene-based olefins as a source for alkylphenol detergents. A big drawback of using polyisobutylene (PIB) as an olefin feed is the need to modify alkylation techniques with specialized alkylation catalysis.

SUMMARY

In one aspect, there is provided a hydroxyaromatic product comprising: an alkyl hydroxyaromatic compound having a structure given by

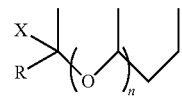

wherein R is a hydroxyaromatic group, X is hydrogen or methyl group and wherein n is 1 or greater.

In another aspect, there is provided an alkyl-substituted hydroxyaromatic compound formed by a process comprising: alkylating a hydroxyaromatic compound with an alkylating agent containing vinylidene-rich propylene oligomers comprising propylene oligomers that terminate with vinylidene double bond, wherein the propylene oligomers are prepared by oligomerizing a propylene-rich feedstock containing olefins wherein at least 50 mol % of the olefins in the feedstock are propylene and wherein at least 50 mol % of the propylene oligomers have the vinylidene double bond.

In yet another aspect, there is provided a lubricating oil composition comprising: a base oil; and a detergent comprising sulfurized alkylphenol, wherein the alkylphenol is made via alkylation with an alkylating agent containing vinylidene-rich propylene oligomers comprising propylene oligomers that terminate with vinylidene double bond, wherein the propylene oligomers are prepared by oligomerizing a propylene-rich feedstock containing olefins wherein at least 50 mol % of the olefins in the feedstock are propylene and wherein at least 50 mol % of the propylene oligomers have the vinylidene double bond.

In still yet another aspect, there is provided a method of alkylating a hydroxyaromatic compound comprising: oligomerizing propylene monomers in presence of single-site catalyst to form vinylidene-rich propylene oligomers comprising propylene oligomers that terminate with vinylidene double bond, wherein the propylene oligomers are prepared by oligomerizing a propylene-rich feedstock containing olefins wherein at least 50 mol % of the olefins in the feedstock are propylene and wherein at least 50 mol % of the propylene oligomers have the vinylidene double bond; and alkylating the hydroxyaromatic compound with the vinylidene-rich propylene oligomers.

BRIEF DESCRIPTION OF DRAWINGS

FIG. 1 shows a graph described in the Examples.

DETAILED DESCRIPTION

The term "olefin" refers to a hydrocarbon that has at least one carbon-carbon double bond that is not part of an aromatic ring or ring system. The term "olefin" includes aliphatic and aromatic, cyclic and acyclic, and/or linear and branched compounds having at least one carbon-carbon double bond that is not part of an aromatic ring or ring system, unless specifically stated otherwise. Olefins having only one, only two, only three, etc., carbon-carbon double bonds can be identified by use of the term "mono," "di," "tri," etc., within the name of the olefin. The olefins can be further identified by the position of the carbon-carbon double bond(s). Depending on the context, the term "olefin" may refer to an "olefin oligomer" or an "olefin monomer."

An "olefin oligomer" is an oligomer made from oligomerization of "olefin monomers." For example, a "propylene oligomer" is made from the oligomerization of nominally propylene monomers. Examples of propylene oligomers include propylene tetramer and propylene pentamer. A "propylene tetramer" is an olefin oligomer product resulting from the oligomerization of nominally 4 propylene monomers. These terms also can be used generically to describe homo-oligomers, co-oligomers, salts of oligomer, derivatives of oligomers, and the like.

An unrefined product of the oligomerization process typically includes a mixture of branched olefin oligomers with a distribution of carbon numbers. The unrefined oligomer products resulting from oligomerization of monomers can be distilled to further isolate or purify the olefin oligomer product to a preferred carbon range.

The term "alkyl" or related term refer to saturated hydrocarbon groups, which can be linear, branched, cyclic, or a combination of cyclic, linear and/or branched.

A "vinylidene-rich propylene oligomers" refers to propylene-based oligomers having a predominance of vinylidene moiety. An olefin oligomer with vinylidene moiety is gem di-substituted at the internal end of the terminal double bond. Conventionally prepared propylene oligomers are typically rich in molecules with tri- or tetra-substituted internal double bond.

As used herein, the term "substituted" means that a hydrogen group has been replaced with an alkyl group, an aromatic group, heteroatom, or a heteroatom-containing group.

It is understood that when combinations, subsets, groups, etc. of elements are disclosed (e.g., combinations of components in a composition, or combinations of steps in a method), that while specific reference of each of the various individual and collective combinations and permutations of these elements may not be explicitly disclosed, each is specifically contemplated and described herein.

The present invention provides compositions and methods related to alkyl-substituted hydoxyaromatic products with highly-structured alkyl groups. More specifically, the present invention describes synthesis of vinylidene-rich propylene oligomers that can be used to synthesize alkyl-substituted hydroxyaromatic products which, in turn, are useful for the production of a wide range of commercial products.

The vinylidene-rich propylene oligomers can be prepared using a single site catalyst. This allows the high vinylidene content oligomers of the present invention to be more reactive in the alkylation reaction and allow for a more efficient synthesis of alkylphenol products.

High vinylidene content can provide numerous benefits over conventional propylene tetramer oligomers. For example, alkylation of phenol with vinylidene-rich propylene oligomers may be accomplished efficiently with reduced olefin to phenol ratios. Other benefits may include lower reaction temperatures, lower batch cycle time, higher conversion rate, and higher para-alkylphenol content.

Vinylidene-Rich Propylene Oligomers

The vinylidene-rich propylene oligomers of the present invention are characterized by a highly ordered structure, featuring a chain with a long linear backbone and regularly-spaced methyl groups.

The vinylidene-rich propylene oligomers of the present invention have an average carbon number ranging from about 9 to about 50. In some embodiments, the average carbon number ranges from 9 to 42, 9 to 39, 9 to 36, or 12 to 32.

The vinylidene oligomers are long straight chain terminal olefins with a branch on every other carbon in the chain starting with the geminal branch on the vinylidene olefin. When numbered from the terminal olefin carbon the branches are on every even numbered carbon in the chain (i.e. branches on carbons 2, 4, 6, and the like) except for the last three carbons the oligomer chain, which may be unbranched or deviate from the regular branching of the remainder of the molecule in other ways, 2,4 dimethyl 1-heptene (trimer), 2,4,6 trimethyl 1-nonene (tetramer), and 2,4,6,8 tetramethyl 1-undecene (pentamer), are examples of vinylidene oligomers of the present invention.

In some embodiments, the vinylidene-rich propylene oligomers are products of oligomerization wherein at least 50 mol % of the oligomers have a vinylidene moiety. In some embodiments, at least 60 mol %, 70 mol %, 80 mol %, 90 mol %, or 95 mol % of oligomers have a vinylidene moiety. Side products of the oligomerization may include oligomers that do not have vinylidene moiety. These oligomers may have other moieties/configurations at the double bond such as tri-substituted, tetra-substituted, vinyl, and di-substituted (cis or trans).

While propylene is the main olefin monomer in the oligomerization reaction, the feed source can have a mixture of olefins having different numbers of carbon atoms, or olefins having predominantly a single number of carbon atoms. The olefins can comprise at least 50 wt. %, at least 55 wt. %, at least 60 wt. %, at least 65 wt. %, at least 70 wt. %, at least 75 wt. %, at least 80 wt. %, at least 85 wt. %, at least 90 wt. %, or at least 95 wt. % of propylene. The monomer may further be introduced to the oligomerization reaction in a mixture with one or more non-olefinic hydrocarbons such as alkanes or aromatics.

In one embodiment, the propylene monomer is sourced from a cracking operation and used without separation of propylene from propane prior to the oligomerization reaction. Such cracking operation may be a catalytic cracking such as Fluid Catalytic Cracking or a thermal cracking such as steam cracking or Coking. In one embodiment, the cracking operation may involve propane dehydrogenation.

The synthesis of vinylidene-rich propylene oligomers may proceed via any known oligomerization method. Synthesis of olefin oligomers or polyolefins are generally known in the related arts. In particular, the synthesis of polyolefins via single-site catalysts is known to provide polymers with highly defined microstructure, tacticity, stereoregularity, and the like.

The vinylidene-rich propylene oligomers of the present invention can be prepared by using compatible single-site catalyst(s) that can control side chain length and/or branching. Single-site catalysts generally fall within two groups: metallocene catalysts and non-metallocene catalysts.

A metallocene is a well-known complex organometallic molecule typically containing zirconium, titanium, hafnium, Group IVA, VA, and VIA transition metals, lanthanide metals, and the like. The metal typically sits at or near the center of the complex and coordinates to two cyclic alkyl anions such as cyclopentadienyl anions. A more detailed discussion of metallocenes can be found in U.S. Pat. No. 6,511,568, which is hereby incorporated by reference. Other suitable metallocenes include ansa-metallocenes and metallocenes and metallocene catalyst systems described in U.S. Pat. No. 8,536,391, which is hereby incorporated by reference.

In one embodiment, the metallocene has a formula

$(RCp)_2MX_2$ wherein Cp is a cyclopentadienyl group and RCp is a substituted cyclopentadienyl group wherein R is an alkyl group or hydrogen, M is Ti, Zr or Hf and X is Cl, Br, I, H, Me, or Et.

Non-metallocene single-site catalysts are typically transition metal catalysts. Transition metal catalysts are described in WO9827124, WO9830612, WO 9623010, EP0816387, which are hereby incorporated by reference. Specific examples of non-metallocene single-site catalysts include Ni, Pd diimine catalyst system, Fe pyridine-diimine catalyst system, 8-quinolinol Ti catalyst system, azetidine titanium catalyst system, chelating diamine catalyst system and the like.

The oligomer product is a propylene oligomer (i.e., the repeating units of the olefin oligomer can be substantially all propylene units). For example, the repeating units of the oligomer can contain at least about 90 mol %, at least 95 mol %, at least 98 mol %, or at least 99 mol % propylene units.

The oligomer product can comprise dimers, trimers, and/or higher oligomers. In some embodiments, the oligomer product can comprise (i) at least 75 wt %, 80 wt %, 85 wt %, 90 wt %, or 95 wt % dimers, trimers, tetramers, pentamers, hexamers, heptamers, octamers, nonamers, and/or decamers; (ii) at least 50 wt %, 55 wt %, 60 wt %, 65 wt %, 70 wt %, 80 wt %, 85 wt %, or 90 wt % trimers, tetramers, pentamers, hexamers, heptamers, octamers, nonamers, and/or decamers; (iii) at least 75 wt %, 80 wt %, 85 wt %, 90 wt %, or 95 wt % dimers, trimers, tetramers, pentamers, hexamers, and/or heptamers; (iv) at least 50 wt %, 55 wt %, 60 wt %, 65 wt %, 70 wt %, 80 wt %, 85 wt %, or 90 wt % trimers, tetramers, pentamers, hexamers, and/or heptamers; (v) at least 30 wt %, 35 wt %, 40 wt %, 45 wt %, 50 wt %, 55 wt %, or 60 wt % dimers, trimers, tetramers, and/or pentamers; (vi) at least 25 wt %, 30 wt %, 35 wt %, 40 wt %, 45 wt %, or 50 wt % trimers, tetramers, and/or pentamers; (vii) at least 25 wt %, 30 wt %, 35 wt %, 40 wt %, 45 wt %, 50 wt %, 55 wt %, or 60 wt % dimers, trimers, and/or tetramers; (viii) at least 20 wt %, 25 wt %, 30 wt %, 35 wt %, 40 wt %, 45 wt %, or 50 wt % trimers and/or tetramers; or (ix) any combination thereof.

In additional or alternative embodiments, the oligomer product can comprise a total of at least 35 wt %, 45 wt %, 45 wt %, 50 wt %, 55 wt %, 60 wt %, or 65 wt % trimer, tetramer and pentamer; alternatively or additionally, a maximum total of 100 wt %, 95 wt %, 90 wt %, or 85 wt % trimer, tetramer and pentamer. In some embodiments, the olefin oligomer can comprise a total of from 35 wt % to 100 wt %, from 40 wt % to 95 wt %, from 45 wt % to 90 wt %, from 40 wt % to 85 wt %, from 50 wt % to 90 wt %, or from 50 wt % to 85 wt %, trimer, tetramer and pentamer.

The oligomer product can comprise less than 40 wt %, 30 wt %, 25 wt %, 20 wt %, 18 wt %, 16 wt %, 14 wt %, 12 wt %, or 10 wt % dimer. Additionally or alternatively, the oligomer product can comprise less than 30 wt %, 25 wt %, 20 wt %, 15 wt %, 10 wt %, 8 wt %, 6 wt %, 5 wt %, 4 wt %, 3 wt %, or 2 wt % oligomer containing 7 or more monomer units.

In some aspects, the oligomer product can comprise at least 50 wt %, 60 wt %, 70 wt %, 75 wt %, 80 wt %, 85 wt %, 90 wt %, or 95 wt % $C_{12}$ to $C_{70}$ (e.g., $C_{12}$ to $C_{40}$, $C_{12}$ to $C_{30}$, $C_{12}$ to $C_{20}$, $C_{14}$ to $C_{70}$, $C_{14}$ to $C_{40}$, $C_{14}$ to $C_{30}$, $C_{14}$ to $C_{20}$, $C_{16}$ to $C_{70}$, $C_{16}$ to $C_{40}$, $C_{16}$ to $C_{30}$, $C_{16}$ to $C_{24}$, $C_{20}$ to $C_{70}$, $C_{20}$ to $C_{40}$, $C_{20}$ to $C_{30}$, or $C_{20}$ to $C_{24}$) oligomers. In some aspects, the oligomer product can comprise less than 30 wt %, 25 wt %, 20 wt %, 15 wt %, 10 wt %, 8 wt %, 6 wt %, 5 wt. %, 4 wt %, 3 wt %, or 2 wt %>$C_{70}$ oligomers. The wt % of the oligomer(s) disclosed herein is based upon the total weight of the oligomer product.

The oligomer product can have a number average molecular weight ($M_n$) in a range from 150 to 10,000 g/mol. For instance, the $M_n$ of the oligomer product or can be at least 150, 250, 325, 400, 500, 600, 650, 700, or 750 g/mol. Additionally or alternatively, the maximum $M_n$ can be 10,000, 7500, 6000, 5000, 4000, 3000, 2500, or 2000 g/mol. Generally, the $M_n$ of the oligomer product can be in a range from any minimum $M_n$ disclosed herein to any maximum $M_n$ disclosed herein.

Heteroatom-Functionalized Oligomers

Depending on the application, the olefin oligomer may be functionalized by reacting a heteroatom-containing group with the olefin oligomer with or without a catalyst. These reactions include hydroxylation, hydrosilation, ozonolysis, hydroformylation, hydroamidation, sulfonation, halogenation, hydrohalogenation, hydroboration, epoxidation, Diels-Alder reactions with polar dienes, Friedel-Crafts reactions with polar aromatics (e.g., hydroxyaromatics), and maleation with activators such as free radical generators (e.g., peroxides).

Exemplary heteroatom-containing groups include alcohols, amines, aldehydes, hydroxyaromatic compounds, sulfonates, acids and anhydrides.

The number of functional groups in the resulting heteroatom-functionalized oligomer can be in a range of 0.60 to 1.2 functional groups per chain (e.g., 0.75 to 1.1 functional groups per chain). The number of functional groups per chain can be determined by any conventional method (e.g., $^1$H NMR spectroscopy).

Alkyl-Substituted Hydroxyaromatic Compounds with Highly-Structured Alkyl Groups

The olefin oligomers described herein may be used to alkylate hydroxyaromatic compounds to form alkyl-substituted hydroxyaromatic compounds. Alkyl-substituted hydroxyaromatic compounds are useful as precursors or end products in a variety of commercial applications.

The alkyl hydroxyaromatic compound may have a structure given by

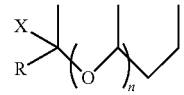

wherein R is a hydroxyaromatic group, X is hydrogen or methyl group and wherein n is 1 or greater. In some embodiments, n is 20 or more less. In some embodiments, n is between 2 and 6.

Useful hydroxyaromatic compounds that may be alkylated include mononuclear monohydroxy and polyhydroxy aromatic hydrocarbons having 1 to 4, and preferably 1 to 3, hydroxyl groups. Suitable hydroxyaromatic compounds (or groups) include phenol, catechol, resorcinol, hydroquinone, pyrogallol, cresol, naphthol, hydroxybenzoic acid, and the like and mixtures thereof and salts thereof (e.g., phenate).

Alkylation of the hydroxyaromatic compound with the olefin oligomer is generally carried out in the presence of an alkylation catalyst. Useful alkylation catalysts include Lewis acids, solid acids, trifluoromethanesulfonic acid, and acidic molecular sieve catalysts. Suitable Lewis acids include aluminum trichloride, boron trifluoride and boron trifluoride complexes (e.g., boron trifluoride etherate, boron trifluoride-phenol and boron trifluoride-phosphoric acid. Suitable solid acids include the sulfonated acidic ion exchange resin type catalysts such as AMBERLYST®-36 (Dow Chemical Company), clay catalysts (e.g. CelaClear F-24X Engineered Clays Corp) or zeolite materials.

The reaction conditions for the alkylation depend upon the type of catalyst used, and any suitable set of reaction conditions that result in high conversion to the alkyl hydroxyaromatic product can be employed. Typically, the reaction temperature for the alkylation reaction will be in the range of from 15° C. to 200° C. (e.g., 85° C. to 135° C.). The reaction pressure will generally be atmospheric, although higher or lower pressures may be employed. The alkylation process can be practiced in a batch wise, continuous or semi-continuous manner. The molar ratio of the hydroxyaromatic compound to the olefin oligomer may be in the range of 10:1 to 0.5:1 (e.g., 5:1 to 3:1).

The alkylation reaction may be carried out neat or in the presence of a solvent which is inert to the reaction of the hydroxyaromatic compound and the olefin mixture.

Upon completion of the reaction, the desired alkyl-substituted hydroxyaromatic compound can be isolated using conventional techniques.

The alkyl group of the alkyl-substituted hydroxyaromatic compound is typically attached to the hydroxyaromatic compound primarily in the ortho and para positions, relative to the hydroxyl group. The alkyl-substituted hydroxyaromatic compound may contain 1 to 99% ortho isomer and 99 to 1% para isomer (e.g., 5 to 70% ortho isomer and 95 to 30% para isomer).

Metal salts of alkylphenols (i.e., phenates) are a useful class of detergent. These detergents can be made by reacting an alkaline earth metal hydroxide or oxide (e.g., CaO, Ca(OH)$_2$, BaO, Ba(OH)$_2$, MgO, Mg(OH)$_2$) with an alkylphenol or sulfurized alkylphenol. When a non-sulfurized alkylphenol is used, the sulfurized product may be obtained by methods well known in the art. These methods include heating a mixture of alkylphenol and sulfurizing agent (e.g., elemental sulfur, sulfur halides such as sulfur dichloride, and the like) and then reacting the sulfurized alkylphenol with an alkaline earth metal base.

Metal salts of alkyl-substituted hydroxyaromatic carboxylic acids are also useful as detergents. Alkyl-substituted hydroxyaromatic carboxylic acids are typically prepared by carboxylation, for example by the Kolbe-Schmitt process, of alkyl-substituted phenoxides.

Non-limiting examples of suitable metals include alkali metals, alkaline earth metals and transition metals. Examples include Li, Na, K, Mg, Ca, Zn, Co, Mn, Zr, Ba, and B.

Many detergent compositions are overbased, containing large amounts of a metal base that is achieved by reacting an excess of a metal compound (e.g., a metal carbonate, hydroxide or oxide) with an acidic gas (e.g., carbon dioxide). Useful detergents can be neutral, mildly overbased, or highly overbased. Processes for overbasing are known to those skilled in the art.

The basicity of the detergents may be expressed as a total base number (TBN). A total base number is the amount of acid needed to neutralize all of the basicity of the overbased material. The TBN may be measured using ASTM D2896 or an equivalent procedure. The detergent may have a low TBN (i.e. a TBN of less than 50 mg KOH/g), a medium TBN (i.e. a TBN of 50 to 150 mg KOH/g) or a high TBN (i.e. a TBN of greater than 150 mg KOH/g, such as 150 to 500 mg KOH/g or more).

The functionalized oligomers and/or derivatized oligomer have uses as lubricating oil additives which can act as dispersants, viscosity index improvers, or multifunctional viscosity index improvers.

The olefin oligomers and their products described herein may be combined with other additives (e.g., detergents, dispersants, oxidation inhibitors, wear inhibitors, friction modifiers, rust inhibitors, viscosity modifiers, pour point depressants, foam inhibitors, and the like to form compositions for many applications, including lubricating oil additive packages, lubricating oils, and the like.

Compositions containing these additives are typically blended into a base oil in amounts which are effective to provide their normal attendant function. Typical amounts of such additives are shown in Table 1 below. The weight amounts in the table below, as well as other amounts mentioned herein, are directed to the amount of active ingredient (that is the non-diluent portion of the ingredient). The weight percent (wt. %) indicated below is based on the total weight of the lubricating oil composition.

TABLE 1

| Compound | Typical, wt. % | Preferred, wt. % |
|---|---|---|
| Detergent | 0.1 to 20 | 0.1 to 8 |
| Dispersant | 0.1 to 20 | 0.1 to 8 |
| Oxidation Inhibitor | 0.1 to 5 | 0.1 to 1.5 |
| Wear Inhibitor | 0.2 to 3 | 0.5 to 1 |
| Friction Modifier | 0.01 to 5 | 0.01 to 1.5 |
| Rust Inhibitor | 0.01 to 5 | 0.01 to 1.5 |
| Viscosity Modifier (solid polymer basis) | 0.1 to 2 | 0.1 to 1 |
| Pour Point Depressant | 0 to 5 | 0.01 to 1.5 |
| Foam Inhibitor | 0.001 to 3 | 0.001 to 0.15 |

Lubricating Oil

The olefin oligomers of the present disclosure may be useful as additives (e.g., as dispersants, detergents, etc.) in lubricating oils to prevent or reduce undesirable ignition events in combustion engines. When employed in this manner, the additives are usually present in the lubricating oil composition in concentrations ranging from 0.001 to 10 wt. % (including, but not limited to, 0.01 to 5 wt. %, 02 to 4 wt. %, 0.5 to 3 wt. %, 1 to 2 wt. %, and so forth), based on the total weight of the lubricating oil composition. If other hydride donors are present in the lubricating oil composition, a lesser amount of the additive may be used.

Oils used as the base oil will be selected or blended depending on the desired end use and the additives in the finished oil to give the desired grade of engine oil, e.g. a lubricating oil composition having an Society of Automotive Engineers (SAE) Viscosity Grade of 0W, 0W-8, 0W-16, 0W-20, 0W-30, 0W-40, 0W-50, 0W-60, 5W, 5W-20, 5W-30, 5W-40, 5W-50, 5W-60, 10W, 10W-20, 10W-30, 10W-40, 10W-50, 15W, 15W-20, 15W-30, or 15W-40.

The oil of lubricating viscosity (sometimes referred to as "base stock" or "base oil") is the primary liquid constituent of a lubricant, into which additives and possibly other oils are blended, for example to produce a final lubricant (or lubricant composition). A base oil, which is useful for making concentrates as well as for making lubricating oil compositions therefrom, may be selected from natural (vegetable, animal or mineral) and synthetic lubricating oils and mixtures thereof.

Definitions for the base stocks and base oils in this disclosure are the same as those found in American Petroleum Institute (API) Publication 1509 Annex E ("API Base Oil Interchangeability Guidelines for Passenger Car Motor Oils and Diesel Engine Oils," December 2016). Group I base stocks contain less than 90% saturates and/or greater than 0.03% sulfur and have a viscosity index greater than or equal to 80 and less than 120 using the test methods specified in Table E-1. Group II base stocks contain greater than or equal to 90% saturates and less than or equal to 0.03% sulfur and have a viscosity index greater than or equal to 80 and less than 120 using the test methods specified in Table E-1. Group III base stocks contain greater than or equal to 90% saturates and less than or equal to 0.03% sulfur and have a viscosity index greater than or equal to 120 using the test methods specified in Table E-1. Group IV base stocks are polyalphaolefins (PAO). Group V base stocks include all other base stocks not included in Group I, II, III, or IV.

Natural oils include animal oils, vegetable oils (e.g., castor oil and lard oil), and mineral oils. Animal and vegetable oils possessing favorable thermal oxidative stability can be used. Of the natural oils, mineral oils are preferred. Mineral oils vary widely as to their crude source, for example, as to whether they are paraffinic, naphthenic, or mixed paraffinic-naphthenic. Oils derived from coal or shale are also useful. Natural oils vary also as to the method used for their production and purification, for example, their distillation range and whether they are straight run or cracked, hydrorefined, or solvent extracted.

Synthetic oils include hydrocarbon oil. Hydrocarbon oils include oils such as polymerized and interpolymerized olefins (e.g., polybutylenes, polypropylenes, propylene isobutylene copolymers, ethylene-olefin copolymers, and ethylene-alphaolefin copolymers). Polyalphaolefin (PAO) oil base stocks are commonly used synthetic hydrocarbon oil. By way of example, PAOs derived from $C_8$ to $C_{14}$ olefins, e.g., $C_8$, $C_{10}$, $C_{12}$, $C_{14}$ olefins or mixtures thereof, may be utilized.

Other useful fluids for use as base oils include non-conventional or unconventional base stocks that have been processed, preferably catalytically, or synthesized to provide high performance characteristics.

Non-conventional or unconventional base stocks/base oils include one or more of a mixture of base stock(s) derived from one or more Gas-to-Liquids (GTL) materials, as well as isomerate/isodewaxate base stock(s) derived from natural wax or waxy feeds, mineral and or non-mineral oil waxy feed stocks such as slack waxes, natural waxes, and waxy stocks such as gas oils, waxy fuels hydrocracker bottoms, waxy raffinate, hydrocrackate, thermal crackates, or other mineral, mineral oil, or even non-petroleum oil derived waxy materials such as waxy materials received from coal liquefaction or shale oil, and mixtures of such base stocks.

Base oils for use in the lubricating oil compositions of present disclosure are any of the variety of oils corresponding to API Group I, Group II, Group III, Group IV, and Group V oils, and mixtures thereof, preferably API Group II, Group III, Group IV, and Group V oils, and mixtures thereof, more preferably the Group III to Group V base oils due to their exceptional volatility, stability, viscometric and cleanliness features.

Typically, the base oil will have a kinematic viscosity at 100° C. (ASTM D445) in a range of 2.5 to 20 mm²/s (e.g., 3 to 12 mm²/s, 4 to 10 mm²/s, or 4.5 to 8 mm²/s).

The present lubricating oil compositions may also contain conventional lubricant additives for imparting auxiliary functions to give a finished lubricating oil composition in which these additives are dispersed or dissolved. For example, the lubricating oil compositions can be blended with antioxidants, ashless dispersants, anti-wear agents, detergents such as metal detergents, rust inhibitors, dehazing agents, demulsifying agents, friction modifiers, metal deactivating agents, pour point depressants, viscosity modifiers, antifoaming agents, co-solvents, package compatibilizers, corrosion-inhibitors, dyes, extreme pressure agents and the like and mixtures thereof. A variety of the additives are known and commercially available. These additives, or their analogous compounds, can be employed for the preparation of the lubricating oil compositions of the invention by the usual blending procedures.

Each of the foregoing additives, when used, is used at a functionally effective amount to impart the desired properties to the lubricant. Thus, for example, if an additive is an ashless dispersant, a functionally effective amount of this ashless dispersant would be an amount sufficient to impart the desired dispersancy characteristics to the lubricant. Generally, the concentration of each of these additives, when used, may range, unless otherwise specified, from about 0.001 to about 20 wt. %, such as about 0.01 to about 10 wt. %.

EXAMPLES

FIG. 1 and FIG. 2 summarize characteristics of the propylene oligomers used in the Examples described herein. The propylene oligomers include conventional propylene tetramer and 5 distillation products of vinylidene-rich propylene oligomers. The distillation products vary in boiling temperatures (FIG. 1) and carbon number (FIG. 2).

The propylene oligomers were tested and analyzed according to the method described in US 2008/0171672A1, which is hereby incorporated by reference. This $^1$H NMR-based method characterized the samples and calculated the average number of branches per molecule, the number of aliphatic and olefin branches per chain.

FIG. 1 shows that distillation products have high vinylidene content and very low tri- and tetra-substituted olefins. FIG. 2 shows that the distillation products have desirable levels of branching while maintaining high vinylidene content.

Alkylphenol Samples

NMR spectroscopy were used to probe branching level of an alkylphenol composition that has been alkylated with various propylene tetramer samples. The alkylphenol NMR data is summarized in Table 2 (proton NMR integrals) below. All NMR data were taken using chloroform as the solvent.

Comparative Example A is an alkylphenol alkylated with a propylene tetramer oligomerized by a conventional method. Comparative Example B is an alkylphenol alkylated with a isomerized alphaolefin. Example 1 is an alkylphenol alkylated with vinylidene-rich propylene oligomer of the present invention.

A key property of the alkylphenols prepared by alkylation of phenol with the propylene oligomers of the present invention is the regularity and high concentration of methyl branching in the alkyl side chain. Aside from the ends of the alkyl chain and the carbon to which the aromatic unit is attached, the alkyl group consists of alternating —$CH_2$— and —CH(R)— groups, where R is methyl when the alkylating agent is propylene oligomer. This structure of the alkyl group, which is likely responsible for some of the desirable properties of the alkylphenol product, gives the product features that allows them to be distinguished from other alkylphenol products through a combination of $^1$H and $^{13}$C NMR spectroscopy.

The alternating $CH_2$ and CH(Me) groups gives the alkyl side chain in alkylphenols according to this invention a higher concentration of methyl groups than is found in side chains in other alkylphenols as illustrated by a higher NMR branching index, which is defined as the ratio of the integrals of the methyl hydrogen resonances to the combined integrals of all aliphatic hydrogen resonances in the molecule. The alkylphenols according to this invention have NMR branching index exceeding 45%. In other words, the integral of methyl resonances constitute more than 45% of the combined integrals for all resonances for protons in the alkyl side chains. More specifically the NMR branching index of the product according to the invention is in the range 45-60%.

While the high concentration of the methyl groups in the alkyl group is a distinguishing feature another equally important distinction is the high concentration of —CH$_2$— groups (methylene groups) placed between two carbons each carrying a methyl substituent —CH(Me)-CH$_2$—CH(Me)-. In $^{13}$C NMR spectra, the resonances for these methylene resonances fall in the range 44-49 ppm, which is further downfield that other $^{13}$C resonances for aliphatic carbons. For alkylphenols according to this invention the resonances in the 44-49 ppm range constitute more than 10% or 15% of all resonances in the aliphatic carbon range 10-50 ppm.

TABLE 2

| Proton NMR Integrals | Comp. Ex. A | Comp. Ex. B | Example 1 |
|---|---|---|---|
| 0.5-0.95 ppm, CH$_3$ | 1 | 1 | 1 |
| 0.95-1.14 ppm, CH$_2$ | 0.9565 | 3.0504 | 0.6975 |
| 1.4-2.1 ppm, CH | 0.4096 | 0.4676 | 0.3765 |
| 2.1-4.0 ppm, Ar—CH | | 0.074 | 0.0417 |
| 4.0-6.0 ppm, C=CH | | | |
| 6.7-6.85 ppm, (Aromatics Ortho to OH) | 0.1529 | 0.1656 | 0.064 |
| 6.0-8.0 ppm (AR—H, not Ortho) | 0.1581 | 0.2504 | 0.0762 |
| Phenolic Protons, app 4.8 ppm | 0.0743 | 0.0831 | 0.0293 |

NMR branching index can be calculated from the NMR data. Table 3 summarizes branching and carbon number information. N$_{aliphatic\ H}$ is the sum of N$_{CH3}$, N$_{CH2}$, and N$_{CH}$. As shown, Example 1 has the highest NMR Branching Index.

TABLE 3

| | Alkyl Group Origin | Comp. Ex. A | Comp. Ex. B | Example 1 |
|---|---|---|---|---|
| NMR Branching Index | N$_{methyl}$/N$_{aliphatic\ H}$ | 42.3% | 22.1% | 48.2% |
| CH$_3$/CH$_2$ | (N$_{methyl}$/3)/(N$_{CH2}$/2) | 0.70 | 0.22 | 0.96 |
| CH$_3$/CH | (N$_{methyl}$/3)/(N$_{CH}$) | 0.81 | 0.71 | 0.89 |
| CH$_3$/(CH$_2$ + CH) | (N$_{methyl}$/3)/(N$_{CH2}$/2 + N$_{C—H}$) | 0.38 | 0.17 | 0.46 |
| CH$_3$/(CH$_3$ + CH$_2$ + CH) | (N$_{methyl}$/3)/(N$_{CH3}$/3 + N$_{CH2}$/2 + N$_{C—H}$) | 0.27 | 0.14 | 0.31 |
| Average alkyl carbon count | (N$_{aliphatic}$ − N$_{phenolic}$)/(2*N$_{phenolic}$) | 15.42 | 26.68 | 34.89 |
| Average alkyl carbon length | (N$_{aliphatic}$ − 0.5*N$_{ortho\ aromatic}$)/(N$_{ortho\ aromatic}$) | 14.97 | 26.78 | 31.91 |
| Average alkyl chain length | | 15.20 | 26.73 | 33.40 |

Carbon NMR results (TABLE 4) comparing alkylphenols with different alkyl groups were obtained. The NMR samples include alkylphenols with conventional tetramer, isomerized oligomer, and vinylidene-rich propylene oligomer. The data was collected with a 400 MHz instrument (100.6 MHz 13C freq.) with a 2 second recycle delay, using chromium acetylacetonate, Cr(acac)$_3$, relaxation agent at 0.05M concentration.

TABLE 4

| | 44-49 ppm integral (A) | 10-50 ppm integral (B) | A/B ratio, % |
|---|---|---|---|
| Comp. Ex. A | 4.76 | 100 | 4.76% |
| Comp. Ex. B | 1.09 | 100 | 1.09% |
| Example 1 | 25.49 | 100 | 25.49% |

All documents described herein are incorporated by reference herein, including any priority documents and/or testing procedures to the extent they are not inconsistent with this text. As is apparent from the foregoing general description and the specific embodiments, while forms of the present disclosure have been illustrated and described, various modifications can be made without departing from the spirit and scope of the present disclosure. Accordingly, it is not intended that the present disclosure be limited thereby.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

Likewise, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

The terms "a" and "the" as used herein are understood to encompass the plural as well as the singular.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

The foregoing description of the disclosure illustrates and describes the present disclosure. Additionally, the disclosure shows and describes only the preferred embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art. While the foregoing is directed to embodiments of the present disclosure, other and further embodiments of the disclosure may be devised without departing from the basic scope thereof, and the scope thereof is determined by the claims that follow.

The embodiments described hereinabove are further intended to explain best modes known of practicing it and to enable others skilled in the art to utilize the disclosure in such, or other, embodiments and with the various modifications required by the particular applications or uses. Accordingly, the description is not intended to limit it to the form disclosed herein. Also, it is intended that the appended claims be construed to include alternative embodiments.

The invention claimed is:

1. A hydroxyaromatic product comprising:
   a highly-structured alkyl hydroxyaromatic compound having a structure given by

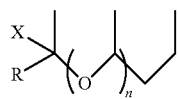

wherein R is a hydroxyaromatic group, X is hydrogen or methyl group and wherein n is 1 or greater; and wherein at least 50 mol % of the alkyl group of the alkyl hydroxyaromatic compound have an alkyl group having a ratio of methyl carbon to methylene carbon of greater than about 0.85.

2. The hydroxyaromatic product of claim 1, wherein R is a phenol group, a hydroxybenzyl group, catechol group, resorcinol group, hydroquinone group, pyrogallol group, cresol group, naphthol group, hydroxybenzoic acid group or a salt thereof.

3. The hydroxyaromatic product of claim 1, wherein n is 20 or less.

4. The hydroxyaromatic product of claim 1, wherein n is between 2 and 6.

5. The hydroxyaromatic product of claim 1, wherein at least 50 mol % of alkyl hydroxyaromatic compound have an alkyl group having an NMR branching index of 45% or greater.

6. The hydroxyaromatic product of claim 1, wherein at least 50 mol % of the alkyl hydroxy aromatic compound have an alkyl group having a ratio of methyl carbon to methylene carbon and methine carbon of greater than about 0.29.

7. The hydroxyaromatic product of claim 1, wherein at least 50 mol % of the alkyl hydroxyaromatic compound have an alkyl group having a ratio of methyl-branch surrounded methylene carbon resonances in 44-49 PPM range as measured in chloroform to combined saturated aliphatic carbon resonances in 10-50 ppm resonances as measured in chloroform of more than 0.15.

8. A lubricating oil composition comprising:
   a base oil; and
   the hydroxyaromatic product of claim 1.

9. A highly-structured alkyl-substituted hydroxyaromatic compound wherein at least 50 mol % of the alkyl group of the alkyl-substituted hydroxyaromatic compound have an alkyl group having a ratio of methyl carbon to methylene carbon of greater than about 0.85 is formed by a process comprising:
   alkylating a hydroxyaromatic compound with an alkylating agent containing vinylidene-rich propylene oligomers comprising propylene oligomers that terminate with vinylidene double bond, wherein the propylene oligomers are prepared by oligomerizing a propylene-rich feedstock containing olefins wherein at least 50 mol % of the olefins in the feedstock are propylene and wherein at least 50 mol % of the propylene oligomers have the vinylidene double bond.

10. The alkyl-substituted hydroxyaromatic composition of claim 9, wherein the hydroxyaromatic compound is phenol, catechol, resorcinol, hydroquinone, pyrogallol, cresol, naphthol, or hydroxybenzoic acid.

11. The alkyl-substituted hydroxyaromatic composition of claim 9, wherein at least 70 mol % of the olefins in the feedstock are propylene.

12. The alkyl-substituted hydroxyaromatic composition of claim 9, wherein the propylene-rich feedstock is prepared by fluid catalytic cracking and oligomerized without prior separation of propane and propylene.

13. The alkyl-substituted hydroxyaromatic composition of claim 9, wherein at least 70 mol % of the propylene oligomers have the vinylidene double bond.

14. The alkyl-substituted hydroxyaromatic composition of claim 9, wherein the propylene oligomers have an average carbon number ranging from about 9 to about 50.

15. The alkyl-substituted hydroxyaromatic composition of claim 9, wherein at least 50 mol % of the composition have an alkyl group with at least 5 carbons.

16. A lubricating oil composition comprising:
   a base oil; and
   a detergent derived from the alkyl-substituted hydroxyaromatic composition of claim 9, wherein the alkyl-substituted hydroxyaromatic composition is sulfurized.

17. The lubricating oil composition of claim 16, wherein at least 70 mol % of the olefins in the feedstock are propylene.

18. The lubricating oil composition of claim 16, wherein the propylene-rich feedstock has an olefin to alkane molar ratio ranging from about 10/1 to about 1/10.

19. The lubricating oil composition of claim 16, wherein the propylene-rich feedstock is isolated from a catalytic or thermal cracking process with a propylene to propane ratio within 5% as produced in the catalytic cracking process without separation of propane and propylene.

20. A method of alkylating a hydroxyaromatic compound to form highly-structured alkyl-substituted hydroxyaromatic compound wherein at least 50 mol % of the alkyl group of the alkyl hydroxyaromatic compound have an alkyl group having a ratio of methyl carbon to methylene carbon of greater than about 0.85, the method comprising:
   oligomerizing propylene monomers in presence of single-site catalyst to form vinylidene-rich propylene oligomers comprising propylene oligomers that terminate with vinylidene double bond, wherein the propylene oligomers are prepared by oligomerizing a propylene-rich feedstock containing olefins wherein at least 50 mol % of the olefins in the feedstock are propylene and wherein at least 50 mol % of the propylene oligomers have the vinylidene double bond; and
   alkylating the hydroxyaromatic compound with the vinylidene-rich propylene oligomers.

21. The method of claim 20, wherein the single-site catalyst is a metallocene.

22. The method of claim 20, wherein the metallocene has a general formula $(RCp)_2MX_2$ wherein Cp is a cyclopentadienyl group and RCp is a substituted cyclopentadienyl group wherein R is an alkyl group or hydrogen, M is Ti, Zr or Hf and X is Cl, Br, I, H, Me, or Et.

23. The method of claim 20, wherein the hydroxyaromatic compound is phenol, catechol, resorcinol, hydroquinone, pyrogallol, cresol, hydroxybenzoic acid or a salt thereof.

\* \* \* \* \*